United States Patent
Cooper et al.

(10) Patent No.: US 9,149,454 B2
(45) Date of Patent: Oct. 6, 2015

(54) USE OF BETHANECHOL FOR TREATMENT OF XEROSTOMIA

(75) Inventors: Nicola Cooper, Cambridge (GB); Julian Clive Gilbert, Cambridge (GB); Robert William Gristwood, Cambridge (GB); Michael Grant Wyllie, Cambridge (GB)

(73) Assignee: Acacia Pharma Limited, Cambridgeshire (GB)

( * ) Notice: Subject to any disclaimer, the term of this patent is extended or adjusted under 35 U.S.C. 154(b) by 0 days.

(21) Appl. No.: 13/505,668

(22) PCT Filed: Nov. 11, 2010

(86) PCT No.: PCT/GB2010/051887
§ 371 (c)(1),
(2), (4) Date: May 31, 2012

(87) PCT Pub. No.: WO2011/058366
PCT Pub. Date: May 19, 2011

(65) Prior Publication Data
US 2012/0232137 A1 Sep. 13, 2012

(30) Foreign Application Priority Data

Nov. 12, 2009 (GB) .................................. 0919822.7
Mar. 17, 2010 (GB) .................................. 1004445.1

(51) Int. Cl.
*A61K 31/27* (2006.01)
*A61K 9/00* (2006.01)

(52) U.S. Cl.
CPC ................. *A61K 31/27* (2013.01); *A61K 9/006* (2013.01); *A61K 9/0056* (2013.01)

(58) Field of Classification Search
CPC ...................................................... A61K 31/27
USPC ........................................................ 514/478
See application file for complete search history.

(56) References Cited

U.S. PATENT DOCUMENTS

| 5,340,821 A | 8/1994 | Abe et al. |
| 2008/0317679 A1 | 12/2008 | Tamarkin et al. |

FOREIGN PATENT DOCUMENTS

| WO | WO-9715296 A1 | 5/1997 |
| WO | WO 98/09623 A2 | 3/1998 |
| WO | WO 98/36733 A2 | 8/1998 |
| WO | WO 2007/092811 A2 | 8/2007 |
| WO | WO-2008100434 A1 | 8/2008 |
| ZA | 9610154 A | 6/1997 |

OTHER PUBLICATIONS

Allen, JR, L.V., "Bethanechol 5-mg/mL Oral Liquid" *International Journal of Pharmaceutical Compounding*, Dec. 2005, vol. 9, No. 6, p. 473.
Chainani-Wu, N. et al., "Assessment of the use of Sialogogues in the Clinical Management of Patients with Xerostomia," *Spec Care Dentist*, 2006, vol. 26, No. 4, pp. 168-174.
Epstein, J.B. et al., "A Clinical Trial of Bethanechol in Patients with Xerostomia after Radiation Therapy," *Oral Surg Oral Med Oral Path*, 1994, No. 77, pp. 610-614.
Jham, B.C. et al., "A Randomized Phase III Prospective Trial of Bethanechol to Prevent Radiotherapy-Induced Salivary Gland Damage in Patients with Head and Neck Cancer," *Oral Oncology*, 2007, vol. 43, pp. 137-142.
Smart, J.D., "Buccal Drug Delivery," *Expert Opin. Drug Deliv.*, 2005, vol. 2, No. 3, pp. 507-517.
Ekström et al. "Secretion From Submucosal Salivary Glands of the Ferret in Response to a Cholinesterase Inhibitor Applied onto the Oral Mucosa." *Eur. J. Oral Sci.* 110.3(2002):230-236.
Hodosh et al. "Treatment of Aphthous Stomatitis with Saturated Potassium Nitrate/Dimethyl Isosorbide." *Quintessence Int.* 35.2(2004):137-141.
Kimura et al. "Relationship Between Nasal Absorption and Physicochemical Properties of Quaternary Ammonium Compounds." *Arch. Int. Pharmacodyn.* 310(1991):13-21.
Restrepo. "Use of Inhaled Anticholinergic Agents in Obstructive Airway Disease." *Respir. Care.* 52.7(2007):833-851.

*Primary Examiner* — Zohreh Fay
(74) *Attorney, Agent, or Firm* — Cooley LLP; Ivor R. Elrifi; Heidi A. Erlacher

(57) ABSTRACT

Bethanechol is administered topically, for the treatment of xerostomia.

10 Claims, No Drawings

USE OF BETHANECHOL FOR TREATMENT OF XEROSTOMIA

CROSS REFERENCE TO A RELATED APPLICATION

This application is a National Stage Application of International Application Number PCT/GB2010/051887, filed November 11, 2010; which claims priority to Great Britain Application Nos. 0919822.7, filed Nov. 12, 2009 and 1004445.1, filed Mar. 17, 2010; all of which are incorporated herein by reference in their entirety.

FIELD OF THE INVENTION

This invention relates to the treatment of salivary gland dysfunction through the topical application of bethanechol to the oral mucosa.

BACKGROUND OF THE INVENTION

Xerostomia can be defined as the subjective sensation of dryness of the mouth. This is usually the result of a decrease in the volume of saliva secreted but may also be due to a change in composition of saliva. Salivary gland hypofunction is defined as demonstrable reduction in either whole or individual gland flow rates. Salivary gland dysfunction has been used as an umbrella term to describe patients with xerostomia and/or salivary gland hypofunction. The prevalence of xerostomia in the general population is between 22-26% and is more common in patients with chronic illness, for example in the palliative care population the prevalence is between 82-83%. The most common cause for salivary gland hypofunction is drug treatment; another cause is Sjogrens syndrome.

Xerostomia is an important condition in cancer patients. In head and neck cancer patients, xerostomia arises from collateral radiation damage to the salivary glands. As many as 95% of head and neck cancer patients suffer significant xerostomia, although head and neck cancer represents less than 5% of all cancers. Xerostomia is also a problem in the broader cancer population. These patients suffer xerostomia principally as a result of the medications they receive. These may include cytotoxic chemotherapy agents such as 5-fluorouracil, paclitaxel, platinum compounds and busulphan, antineoplastic hormonal agents including anastrozole and bicalutamide; and concomitant medications not specifically given for cancer but common especially in advanced cancer patients, such as anti-depressants, opioid painkillers, antihistamines, corticosteroids, H2 blockers, hypnotics and many others. Xerostomia has been reported to be the fourth commonest side-effect of chemotherapy and the third most distressing (Zanni, Pharmacy Times August, 2007). In one study of breast cancer patients undergoing adjuvant chemotherapy, 44% were found to have significant hypofunction of salivary glands and 39% complained of xerostomia one year after chemotherapy (Jensen et al., 2008. Oral Oncology 44:162-173). In bone marrow transplant patients, impairment of salivary gland function, with a dramatic reduction in salivary flow has been seen one month after transplant, with only partial recovery after 4 months (Jacobson et al. 1996, Oral Surg Oral Med Oral Pathol Oral Radiol Endod, 81:38-43). By damaging salivary gland cells, chemotherapeutic agents may affect both the volume of saliva produced and its composition.

In advanced cancer patients, i.e. those with cancer considered to be incurable, palliative chemotherapy is often used to improve quality and duration of life. In addition to any xerostomia caused by such chemotherapy, such patients may well have to contend with the effects of advancing age, which can on its own contribute to a reduction of up to 40% in salivary flow, as well as multiple other xerostomic medications. In one study of 120 advanced cancer patients, 117 were receiving other medications known to cause xerostomia, with the median number of such drugs being 4 per patient (Davies et al. 2002, Oral Oncology, 38:680-685). In that series, 82% had abnormally low unstimulated whole salivary flow rate and 78% reported xerostomia. Another published series of 99 consecutive advanced cancer patients reported an 88% rate of dry mouth (Oneschuk et al. 2000, Support Care Cancer 8:372-376).

The management of salivary gland hypofunction involves treatment of the cause, symptomatic treatment and treatment of the complications. Symptomatic treatment involves the use of saliva substitutes or saliva stimulants.

A number of pharmacological agents have been used as salivary stimulants, including yohimbine and nicotinamide. The most widely used are parasympathomimetic drugs, choline esters or anticholinesterase drugs. The most well known is pilocarpine which acts primarily on muscarinic receptors. Muscarinic agonists when administered systemically tend to produce side effects including sweating and cardiovascular changes.

Bethanechol chloride, also called carbamyl-methylcholine chloride, is a known drug which has been used clinically for many years. It is available in tablets and as an injection and is used as a stimulant of the smooth muscle of the gastrointestinal tract, and in particular the urinary bladder. It can also be of value in certain cases of postoperative abdominal distension and gastroparesis. It is administered orally, preferably on an empty stomach in order to minimise nausea and vomiting. For the treatment of acute post-operative or post-partum non-obstructive urinary retention or neurogenic atony of the bladder with retention, an oral dosage of 10-50 mg of bethanechol chloride 3-4 times daily is recommended.

It has been reported that bethanechol chloride given at 25 mg four times a day can cause significant side-effects, such as abdominal cramping, blurred vision, fatigue and an increase in urinary frequency. The drug has also been administered by subcutaneous injection, however, parenteral dosage forms are no longer available in the USA. It has been reported that a severe cholinergic reaction is likely to occur if it is given by the i.v. or i.m. routes. Severe reactions have also been reported after subcutaneous injection. Bethanechol is contraindicated in patients with hyperthyroidism, peptic ulcer, latent or active bronchial asthma, coronary artery disease, mechanical obstruction of the GI tract or bladder neck, marked vagotonia, epilepsy, parkinsonism, spastic GI disturbances, peritonitis or acute inflammatory conditions of the GI tract, pronounced bradycardia or hypotension or vasomotor instability. The safety and efficacy of bethanechol in pediatric patients have not been established.

Bethanechol administered orally has been tested in the treatment of xerostomia in a small number of clinical studies. The drug has been reported to increase salivary flow. Available data suggest that effects on salivation are dose-related, up to the maximum dose which may be safely administered via the oral route. In one study in patients with head and neck cancer-associated xerostomia, it was reported that of a total of 55 patients who were considered for enrolment, 12 (22%) were not eligible to take oral bethanechol due to systemic conditions (Jham et al. 2007, Oral Oncol. 43:137-142).

One potential way to increase efficacy and yet avoid further side-effects could be to give drugs by topical application to the oral mucosa in order to directly target the underlying minor salivary glands. For this to work the drug must be able to cross the oral mucosal membrane. The concept of buccal drug delivery is well known and a number of reviews on the subject have been published; see for example Buccal Drug Delivery by John Smart (2005), Expert Opin. Drug Deliv., 2(3):507-517. In the abstract of this article, it concludes that "The buccal mucosa, however, while avoiding first pass effects is a formidable barrier to drug absorption". And later "Currently this route is restricted to the delivery of a limited number of small lipophilic molecules that readily cross the buccal mucosa". In general, drug permeability across buccal tissue is dependent upon physicochemical properties of the drug, such as lipophilicity, molecular weight, and degree of ionisation at physiological pH. There are two possible route of absorption through the squamous stratified epithelium of the oral mucosa, these being transcellular (intracellular, passing through the cell) and paracellular (intercellular, passing around the cell). Permeation has been reported to be mainly by the paracellular route through the intracellular lipids produced by membrane-coating granules; however, the route taken depends upon the physicochemical properties of the drug. Generally small molecules that are predominantly lipophilic, with a Log P range of 1.6-3.3, are absorbed most rapidly, and most drugs delivered successfully via the buccal or sublingual route are lipophilic. A compound with a Log P value of less than 0 or less than 1 is usually considered too hydrophilic to be a drug candidate, particularly if it needs to cross lipophilic biological membranes for its activity.

Chemically, bethanechol chloride is a quaternary ammonium compound, it is very polar in nature and has a high aqueous solubility (hydrophilic) and a calculated log P value of around −4.0. This is one of the lowest values reported in the literature for a clinically used pharmaceutical agent. Consistent with these physicochemical properties, bethanechol does not significantly penetrate into the CNS at therapeutic doses and is only poorly absorbed from the GI tract.

SUMMARY OF THE INVENTION

This invention relates to the use, preferably in man, when administered locally to the oral mucosa, of bethanechol, e.g. as the chloride, for the treatment of xerostomia. When so administered in certain formulations, and even at doses below those known to be associated with side-effects when administered orally, bethanechol chloride is unexpectedly found to be an effective treatment of the condition. This is especially surprising, given that the physicochemical properties of bethanechol chloride are such that it is very difficult to consider using the drug for topical applications where passage of the drug across mucosal membranes would be required for activity. This is particularly the case for topical use in the treatment of xerostomia whereby penetration of bethanechol across buccal mucosal membrane would be required for the drug to reach underlying salivary glands.

According to a further aspect of the invention, a novel formulation is in the form of a package containing, and from which can be dispensed, a liquid or semi-solid formulation comprising bethanechol.

DESCRIPTION OF THE INVENTION

For the purpose of the present invention, bethanechol is typically administered via the buccal route with the intention of providing a direct action on the salivary glands, thus resulting in an improvement of conditions associated with xerostomia. In one embodiment of the invention, the administered dose of bethanechol is held within the buccal cavity for a specified period of time in order to facilitate a local action on the minor salivary glands. The buccal contents are then swallowed such that any drug not absorbed through the buccal mucosa has the opportunity to gain entry to the systemic circulation via gastrointestinal absorption, and this achieves a secondary stimulation of salivary flow including from the major glands. The period of time that the formulation is held in the mouth before swallowing may be from 30 seconds to 5 minutes, preferably 1 to 3 minutes, more preferably 2 minutes.

A formulation of the invention is typically in a single unit dose form. It may be packaged as, e.g. a sachet, vial, blow-fill seal container, multidose container with separate doses administered manually, for example using a syringe, multidose container with unit dose dispenser, e.g. unidose pump or spray, semi-solid in tube, from which an appropriate amount can be extruded. The formulation, which will typically be sterile, for therapeutic use, preferably comprises a self-preserving system (e.g. ethanol or other alcohol) and/or includes an appropriate preservative.

When it is intended that the bethanechol is swallowed after a residence time in the buccal cavity, the dosing volume for a liquid or semi solid formulation is typically between 0.1 ml and 1.0 ml, preferably 0.25 ml to 0.75 ml, more preferably 0.3 ml to 0.6 ml.

In order to facilitate the bethanechol reaching the minor salivary glands, the bethanechol may be present in the formulation as a saturated solution.

There is a range of delivery systems for delivery of drugs to the buccal mucosa (see Smart 2005; this reference is incorporated herein in its entirety). These include buccal bioadhesive systems which may be tablets, patches, films, semisolids, liquids and particulates. Semi-solid formulations include gels and ointments. Appropriate dosage levels may be determined by any suitable method known to one skilled in the art. Preferable doses (single administration) of bethanechol chloride are in the range of 1 mg to 50 mg, preferably 2 mg to 25 mg and more preferably 3 mg to 9 mg. More than one administration may be given each day. It may be advantageous to combine or co-administer a product of the invention with other classes of drug. Drugs which may be co-administered include, but are not limited to, acetylcholinesterase inhibitors.

The following studies may provide evidence for the utility of the present invention.

Preclinical Studies

In the experiments outlined below, bethanechol chloride for buccal administration was prepared as a saturated solution in a solvent mixture comprising PEG 400, glycerol, ethanol and sodium phosphate buffer. Specific solvent amounts were 30% PEG 400, 30% glycerol, 20% ethanol with 20% phosphate buffer (formed by mixing 50 ml of 0.1M sodium phosphate monobasic (monohydrate) with sufficient 0.1M sodium phosphate dibasic (heptahydrate) until a pH of 5.5 was achieved). Bethanechol chloride was present at up to 33%.

In order to prepare a saturated solution of bethanechol chloride the following method was used. A magnetic flea was placed into a 20 ml scintillation vial and the weight of both was recorded. Exactly 0.8 g of the pH 5.5 buffer solution was placed into the container. Bethanechol chloride was gradually added into the container while allowing time for the bethanechol to dissolve into the buffer until a saturated solution was achieved. It was found necessary to add an additional 0.235 g of buffer to ensure formulation of a mobile suspension of bethanechol. Once the saturated solution (containing un-dissolved bethanechol) had been achieved, the vial was placed onto a balance and the total weight recorded. The weight of the magnetic flea and empty vial was deducted from the total weight to obtain the final weight of the saturated solution. This weight represents 20% of the final formulation. The amounts of ethanol, glycerol and PEG 400 were calculated to make a solution containing 30% PEG 400, 30% glycerol, 20% ethanol and 20% buffer and bethanechol. The solution was then mixed using the magnetic flea for 30 minutes at room temperature. In order to ensure saturation, two further aliquots of bethanechol chloride were added with further mixing, resulting in a viscous clear solution with a small amount of undissolved bethanechol being present. The pH of the final formulation was 6.7.

In an efficacy study, male Sprague-Dawley rats (350-400 g) were anaesthetized with pentobarbitone 40 mg/kg i.p. After 15-30 min, a Parafilm ball was inserted into the back of the oral cavity to prevent the loss of solution and saliva into the esophagus and airways. At T−10 a cotton wool ball was inserted into the oral cavity and 10 minutes later removed wiping excess saliva. At T=0 min drug or vehicle were instilled into the oral cavity using a pipette. Ten microlitres was instilled on one side of the mouth and ten microlitres on the other. At T plus 20 min another cotton wool ball was inserted into the oral cavity, and 10 minutes later it was removed wiping excess saliva. The next ball was inserted and this removed after 10 minutes and the procedure repeated for up to 70 minutes. The amount of saliva in the ball was calculated by subtraction of the initial ball weight from the final weight after removal from the buccal cavity.

The results showed that bethanechol when applied topically caused a sustained and significant increase in salivary output for up to 70 minutes. Saliva production data were analyzed by repeated measures two-way ANOVA followed by Bonferronis post tests (GraphPad Prism version 5.0, GraphPad Software, San Diego, Calif., USA). The total saliva production data and the area under the curves of saliva production were analyzed by a one-way ANOVA followed by a Dunnett's multiple comparison test or and unpaired Student's t test (GraphPad Prism). Bethanechol increased the total saliva production during the 70 minute collection period by 72% above vehicle effect and this was significant at P less than 0.01 (n=4).

In separate experiments, the effects of bethanechol (saturated solution, see above) were compared with those of physostigmine (1% solution in saline) on cardiovascular and respiratory parameters when applied to the buccal cavity of rats. Anaesthesia was induced in animals with urethane (1.75 g/kg given i.p.). Each animal was artificially ventilated via a tracheal cannula that was connected to a Fleisch (size 00) pneumotachograph and a pressure transducer (pressure range ±2 cm H2O). Changes in pulmonary inflation pressure were recorded using a lung function data acquisition system (Powerlab, AD Instruments) and displayed in real time on a personal computer. The left carotid artery was cannulated for recording blood pressure and heart rate, and the left jugular vein cannulated for drug administration. For topical administration, after 15-30 minutes a Parafilm ball was inserted into the back of the oral cavity to prevent the loss of solution into the esophagus and airways. At T−10 minutes a cotton wool ball was inserted into the oral cavity and 10 minutes later it was removed and excess saliva wiped away. At T=0 minutes physostigmine (1%, 10 microlitres each on left and right sides) or bethanechol (10 microlitres each on left and right sides) were instilled using a pipette. At T=10 minutes, another cotton wool ball was inserted into the oral cavity, 10 min later, it was removed and the excess saliva wiped away. The effects on baseline cardiovascular and respiratory parameters were recorded over 90 minutes. Physostigmine produced changes in all measured parameters, the mean maximum effects seen during the observation period were for pulmonary inflation pressure 44% increase, mean arterial pressure 17% decrease and heart rate 9.3% decrease (all n=2). In contrast, bethanechol produced minimal (and not significant) effects on any of these parameters, the mean maximum changes being 0% change, 3% decrease and 1% decrease for pulmonary inflation pressure, mean arterial pressure and heart rate respectively (n=3).

For an additional comparison, the effects of bethanechol (prepared in saline, dosing volume 0.1 ml) over a dose range of 0.3 micrograms/kg to 300 micrograms/kg administered intravenously were studied in rats. Doses were administered in ascending order to each animal (n=3) and cardiovascular and respiratory effects monitored over 5 minutes or until the recorded parameter had returned to baseline (whichever was the later). Bethanechol even at the lowest administered dose of 0.3 micrograms/kg produced significant decreases in mean arterial pressure (31% decrease) and heart rate (6% decrease), whilst increases in pulmonary inflation pressure were seen at 3 micrograms/kg and above. The effects observed with bethanechol at 300 micrograms/kg were mean arterial pressure 72% decrease, heart rate 69% decrease and pulmonary inflation pressure 30% increase. These data, along with the efficacy data shown above, indicate that topically applied bethanechol can achieve stimulation of salivary flow without producing untoward systemic effects due to buccal absorption. In contrast, the data indicate that physostigmine is sufficiently well absorbed through the buccal mucosa to produce adverse effects.

Clinical Study

A cohort of approximately 20 patients with xerostomia is randomized to receive either placebo or bethanechol formulation or vice versa with at least 3 days washout between the treatment segments. Each treatment is given as a small volume (approximately 0.5 ml) solution to be retained against the buccal mucosa for 1 to 2 minutes and then swallowed. Clinical investigations include vital signs, hematology/chemistry and appearance of the buccal mucosa. Efficacy measurements include salivary flow and composition of major and minor glands using standard techniques (see e.g. Ferguson 1999, Archives of Oral Biol., 44: S11-S14; Boros etal., Archives of Oral Biol., 44: S59-S62) and the assessment of subjective oral dryness/comfort using validated measures (see e.g. Chainani-Wu et al., 2006, Spec. Care Dentist 26(4): 164-170). Bethanechol is shown to increase salivary flows and to improve subjective oral dryness/comfort scores.

The invention claimed is:

1. A method for treating xerostomia, wherein said method comprises buccal administration of bethanechol to a subject in need of such treatment, wherein the bethanechol is administered as a liquid solution containing between 2-25 mg of bethanechol in 0.1-1.0 ml of solution per administration, administered more than once each day, wherein the bethanechol is maintained in the buccal cavity for between 30 seconds-5 minutes and is then swallowed.

2. The method according to claim 1, wherein the xerostomia is associated with head and neck cancer.

3. The method according to claim 1, wherein the xerostomia is associated with drug treatment.

4. The method according to claim 1, wherein the xerostomia is associated with cancer chemotherapy treatment.

5. The method according to claim 1, wherein the xerostomia is associated with Sjogren's syndrome.

6. The method according to claim 1, wherein the xerostomia is associated with late-stage cancer.

7. The method according to claim 1, wherein the bethanechol is in the form of bethanechol chloride.

8. The method according to claim 1, wherein the bethanechol is in the form of the S-enantiomer.

9. The method according to claim 1, wherein the bethanechol is maintained in the buccal cavity from 1 to 3 minutes prior to being swallowed.

10. The method according to claim 9, wherein the bethanechol is maintained in the buccal cavity for 2 minutes prior to being swallowed.

* * * * *